(12) United States Patent
Lipovetsky et al.

(10) Patent No.: US 11,141,246 B2
(45) Date of Patent: Oct. 12, 2021

(54) TIP FOR AN INTRAORAL SCANNER

(71) Applicant: Shlomo Lipovetsky, Rishon Lezion (IL)

(72) Inventors: Shlomo Lipovetsky, Rishon Lezion (IL); Sophie Tankus, Bat Yam (IL); Ronen Dekalo, Gan Hadarom (IL)

(*) Notice: Subject to any disclaimer, the term of this patent is extended or adjusted under 35 U.S.C. 154(b) by 521 days.

(21) Appl. No.: 15/813,762

(22) Filed: Nov. 15, 2017

(65) Prior Publication Data

US 2018/0071061 A1 Mar. 15, 2018

Related U.S. Application Data

(63) Continuation-in-part of application No. PCT/IL2016/050508, filed on May 15, 2016.

(30) Foreign Application Priority Data

May 18, 2015 (IL) .......................................... 238888

(51) Int. Cl.

| A61C 9/00 | (2006.01) |
|---|---|
| A61B 1/247 | (2006.01) |
| A61B 1/24 | (2006.01) |
| A61C 17/022 | (2006.01) |
| A61C 17/02 | (2006.01) |
| A61C 19/04 | (2006.01) |

(52) U.S. Cl.
CPC .............. *A61C 9/0053* (2013.01); *A61B 1/24* (2013.01); *A61B 1/247* (2013.01); *A61C 9/0033* (2013.01); *A61C 17/022* (2013.01); *A61C 17/0202* (2013.01); *A61C 19/043* (2013.01)

(58) Field of Classification Search
CPC ...... A61C 9/0053–0073; A61C 17/022; A61C 1/16; A61C 3/02; A61C 3/025; A61C 9/0033; A61C 9/004; A61C 9/0046; A61C 9/0086; A61C 17/02; A61C 17/0202; A61B 1/24; A61B 1/253
See application file for complete search history.

(56) References Cited

U.S. PATENT DOCUMENTS

| 4,184,175 A | 1/1980 | Mullane, Jr. |
| 5,178,536 A * | 1/1993 | Werly ...................... A61B 1/24 |
| | | 348/66 |

(Continued)

FOREIGN PATENT DOCUMENTS

| JP | 2004267671 A | 9/2004 |
| WO | 2015/038376 A1 | 3/2015 |

OTHER PUBLICATIONS

International Search Report for PCT/IL2016/00508, 3 pages, dated Aug. 21, 2016.

(Continued)

*Primary Examiner* — Edward Moran

(57) ABSTRACT

A tip for an intraoral scanner, the tip having a housing body, including an imaging unit through which images are transferred to an imaging module of the intraoral scanner, one or more apertures adapted to provide gas streams therethrough and configured such that the oral region is cleansed from blood or oral particles by the gas streams prior to scanning the oral region by the imaging unit, while during the scanning the gas streams diffuse around the periphery of the oral region.

6 Claims, 3 Drawing Sheets

(56) References Cited

U.S. PATENT DOCUMENTS

| | | | |
|---|---|---|---|
| 5,921,776 A * | 7/1999 | Heilbrunn | A61C 1/16 |
| | | | 433/116 |
| 6,386,867 B1 | 5/2002 | Durbin | |
| 7,494,338 B2 * | 2/2009 | Durbin | A61C 9/00 |
| | | | 433/29 |
| 2002/0064752 A1 | 5/2002 | Durbin et al. | |
| 2003/0232302 A1 | 12/2003 | Babayoff et al. | |
| 2006/0154198 A1 | 7/2006 | Durbin et al. | |
| 2010/0145189 A1 | 6/2010 | Hintersehr | |
| 2018/0132980 A1 * | 5/2018 | Weisenberg | B33Y 50/00 |

OTHER PUBLICATIONS

Written Opinion of the International Searching Authority for PCT/IL2016/00508, 5 pages, dated Aug. 21, 2016.

* cited by examiner

TIP FOR AN INTRAORAL SCANNER

FIELD OF THE INVENTION

The present invention relates to the field of intraoral scanners. More particularly, the invention relates to an enhanced tip or mouthpiece for an intraoral scanner.

BACKGROUND OF THE INVENTION

Scanners to determine the surface contour of objects by non-contact imaging methods has become increasingly important in many applications including the in vivo scanning of dental structures to create a three-dimensional (3D) model. Such scanning devices, such as intraoral scanners have been developed and made commercially available for the dental market, and have been described in the patent literature incorporating a variety of technologies and configurations.

Unfortunately, for such intraoral scanners it has proven to be difficult to collect valid three-dimensional measured or scanned data of the jaw and/or teeth, for example because there are regions in the oral cavity that conceal the view of the sub-gingival or that are contaminated with blood and saliva.

An attempt to overcome this problem is suggested by US 2010/0145189, which discloses an intraoral scanner for collecting three-dimensional measured or scanned data of the jaw or teeth, which accommodates a scanning unit in a front region leading into the oral region and which at this front region also accommodates an air delivery device through which pressurized air may be locally supplied in the oral region. However, in the configuration of the proposed scanner, the air delivery device becomes ineffective as while it tries to reveal the concealed region with the pressurized air, it covers the optical element at the edge of the scanner's tip with in mouth particles (e.g., blood, saliva and other residues located within the oral cavity of the patient).

US 2006/0154198 discloses a 3D dental scanner. However, this scanner suffers from major drawbacks. First, in order for optically imaging a dental structure within an oral cavity, it is required to move one or more image apertures on an arm coupled to a fixed coordinate reference frame external to the oral cavity. Another major drawback is that in the configuration of this scanner, the air delivery device becomes ineffective as the formation of the pressurized air lacks the ability to prevent the covering of the optical element of the scanner with in mouth particles. The lack of ability to maintain the exposed optical element in a clean and dry condition during a scanning session is a major drawback from which such prior-art scanners are suffered from.

It is an object of the present invention to provide a device which is capable of performing an accurate scanning that includes the sub-gingival.

It is another object of the present invention to provide a device which is capable of enabling to provide a precise data collection and transmission of the scanned intraoral region.

It is yet another object of the present invention to provide a device that enables to create a correct 3D model the intraoral region of a subject.

It is a further object of the present invention to provide a device that enables to obtain an optimal partial denture that may result in long lasting healthy gum and tooth.

It is another object of the present invention to provide a device that is capable of cleaning and drying an intraoral region prior to the scanning.

It is still an object of the present invention to provide a device which is capable of revealing covered teeth portions while applying in vivo scanning of dental structures to create a 3D model, while maintaining exposed parts of an imaging unit in a clean and optimal condition (e.g., maintain exposed elements of an optical scanner such as lens and a mirror from oral particles and with no moisture or vapor).

Other objects and advantages of the invention will become apparent as the description proceeds.

SUMMARY OF THE INVENTION

The present invention relates to a tip for an intraoral scanner, comprising: a housing body having an imaging unit through which images are transferred to an imaging module of the intraoral scanner, at least one aperture adapted to provide gas streams, wherein said at least one aperture is configured such that during a scanning session a scanned region is first being cleaned and dried (e.g., from blood or other oral particles) by gas streams, prior to the actual scanning of said region by said imaging unit, while after the cleaning and drying during the actual scanning of said region, said at least one aperture causes gas streams to diffuse around the entire periphery of said cleaned and scanned region.

According to an embodiment of the invention, the at least one aperture includes at least one adjustable leading nozzle adapted to provide air streams for cleaning and drying a region of a portion of a tooth prior to its scanning by the imaging unit, and at least one secondary/maintaining sub-gingival exposing adjustable nozzle adapted to cause air stream to diffuse around the entire periphery of said tooth, preserving after the cleaning and drying of said region, and gingival retraction.

According to an embodiment of the invention, the tip further comprises a buffering wall adapted for preventing the spread of oral particles to reach the imaging unit during the cleaning, wherein said buffering wall at least partially surrounds the location of the imaging unit.

According to an embodiment of the invention, the tip further comprises an absorbing layer adapted to capture oral particles during the cleaning of the scanned region, wherein said absorbing layer is located on the housing in such a way that during the scanning session it faces toward the scanned region. The absorbing layer can be disposable and/or replaceable. The absorbing layer can be made of a flexible material (e.g., sponge), semi-rigid material or rigid material.

According to an embodiment of the invention, the gas can be air, mixture of other gases or any other type of suitable gas.

According to an embodiment of the invention, the housing includes a connector to which at least one pressurized gas source is connected to supply the gas streams to the at least one aperture via one or more ducts or canals that transfers said gas from said source to said at least one aperture.

In another aspect, the present invention relates to a method of performing a dental scan, said method comprising providing an intraoral scanner equipped with a tip configured to scan an intraoral region by enabling to clean the intraoral region prior to the actual scanning of said region, and while during the scanning of said region, causing gas streams to diffuse around the entire periphery of said region, thereby enabling to perform a scanning procedure on a subject or patient by first cleaning each intraoral region.

DETAILED DESCRIPTION OF THE INVENTION

Figure 1:
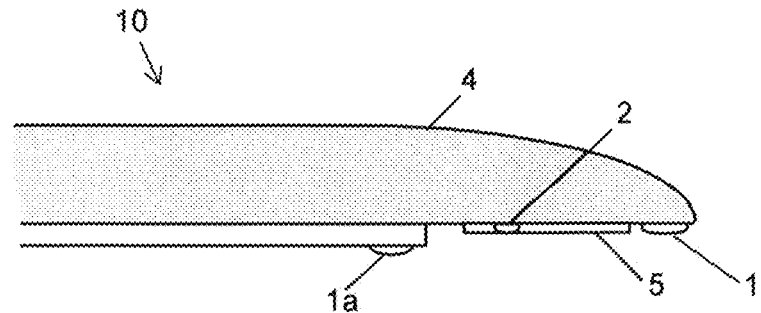
FIG. 1 schematically illustrates a side view of a tip for an intraoral scanner, according to an embodiment of the invention.

Reference will now be made to several embodiments of the present invention, examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

The terms, "for example", "e.g.,", "optionally", as used herein, are intended to be used to introduce non-limiting examples. While certain references are made to certain example system components or services, other components and services can be used as well and/or the example components can be combined into fewer components and/or divided into further components.

The present invention is a tip for an intraoral scanner that includes a housing body having an imaging unit (e.g., an optical arrangement that may include lenses, mirrors, etc.) through which images are transferred to an imaging module of the intraoral scanner and at least one aperture configured to control the direction and characteristics of gas streams in two stages. One stage is used to maintain the imaging unit in a clean condition, and the other stage is used to reveal the concealed portion of a tooth or jaw during the actual scanning session. According to an embodiment of the invention, the at least one aperture is configured such that during a scanning session an intraoral region is first being cleaned and dried while maintaining the imaging unit in a clean condition (e.g., from blood or other oral particles) by applying gas streams directed at that region, prior to the actual scanning of that intraoral region by the imaging unit, while after the cleaning and during the actual scanning of that region, the at least one aperture causes gas streams to diffuse around the entire periphery of the cleaned region by retracting gingiva.

According to an embodiment of the invention, the at least one aperture is configured in such a way that it enables to form two separate stages, in which each stage performs a different action on a scanned intraoral region during a scanning session in terms of timing and location of the supplied gas streams:

A pre-scanning stage that cleans and dries that region in way that maintains the exposed elements of the imaging unit (e.g., an outer lens or a transparent medium) in a maximal/optimal cleaning condition. According to an embodiment of the invention, this can be achieved by using at least one leading nozzle that is adapted to apply gas streams that are directed toward that region and which are generally perpendicular with respect to the top crown surface of a tooth; and A sub-gingival exposing stage in which one or more sub-gingival exposing secondary nozzles are used to diffuse gas stream around the entire periphery of the cleaned region by retracting gingiva during the actual scanning of that region, thereby enabling to reveal the concealed portion of a tooth or jaw. The sub-gingival exposing stage also maintains the scanned area clean and dry.

According an embodiment of the invention, both stages can be achieved by a single aperture that runs along the housing body, in such a way that a portion of this aperture is used as a leading nozzle that forms the pre-scanning stage and other portion (or portions) of it is used as a secondary/sub-gingival exposing nozzle (or nozzles) that forms the sub-gingival exposing stage. For example, an approximate portion of the aperture (with respect to the length of the tip) may function as a leading nozzle that forms the pre-scanning stage and a distal portion of the aperture (with respect to the length of the tip) may function as a sub-gingival exposing nozzle(s) that forms the sub-gingival exposing stage. In such embodiment, the distal portion may at least partially surround the exposed elements of the imaging unit while the proximate portion may be located prior to the location of the imaging unit.

Figure 2:
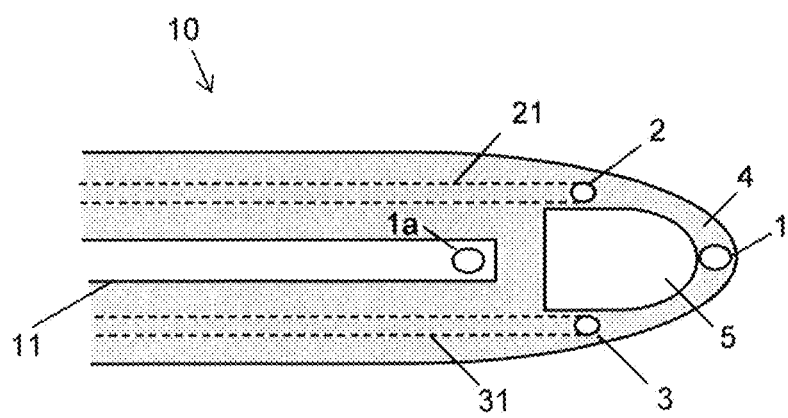
FIG. 2 schematically illustrates a bottom view of the tip of FIG. 1.

FIGS. 1 and 2 show a device that can be used in conjunction with the invention. The device illustrated in these figures is particularly convenient because it can be applied as an ad-on device to existing intraoral scanners without the need to carry out major alterations in the structure. The device generally indicated by numeral 10 in the figure comprises a housing body 4 having an imaging unit 5 through which images are transferred to an imaging module of an intraoral scanner (not shown), at least one leading nozzle 1 and one or more sub-gingival exposing nozzles 2 and 3. Each of the nozzles 1, 2 and 3 is adapted to deliver pressurized gas (e.g., air) through it via ducts or canals (as indicated by numerals 11, 21 and 31, respectively) that may receive the gas from a gas source, which can be either an autonomous operated gas source or other operated form of external gas source. Device 10 includes a connector or other arrangement adapted to connect the gas source to the ducts or canals. The dotted lines 21 and 31 in FIG. 2 indicate a possible form and location of the ducts or canals within the body 4 of device 10. According to an embodiment of the invention, the external gas source may supply the air to all the nozzles simultaneously. According to another embodiment, the gas can be supplied to the leading nozzle and to secondary/sub-gingival exposing nozzles separately, thereby enabling to control the timing of the gas streams at each stage.

According to one embodiment, an autonomous gas source is used to automatically control the supply of the required form of gas streams (e.g., by controlling the velocity and intensity of the gas streams). The autonomous gas source can be controlled according to the distance of the tip from objects located in the mouth of a person (e.g., such as tooth or gingiva). For example, readings from one or more of the sensors located at the tip can be used to determine the distance of the tip from the in-mouth object, and accordingly the autonomous gas source adjusts the velocity/intensity of the supplied gas streams. In one embodiment, the sensors are adapted to provide range or distance measurements, such as infra-red (IR) sensors or other optical sensors. In another embodiment, images from the imaging module of the intraoral scanner can be analyzed in real-time in order to detect the distance between an oral object and the tip (e.g., by applying suitable computer vision algorithms) and be used as an input (in terms of distance) to the autonomous gas source in order to be able to adjust the supply of the gas streams (e.g., in terms of velocity or intensity).

According to an embodiment of the invention, device 10 is used as a tip (i.e., a mouthpiece) of an intraoral scanner, which is adapted to be inserted into an oral region in order to collect 313 measured or scanned data. In another embodiment, device 10 can be provided as an integral part of an intraoral scanner.

During operation, device 10 is positioned, for example, upwardly to perform a scan of an upper dental arch, and the device may then be rotated approximately 180° to face downward for scanning, for example, the lower dental arch. The device 10 may move laterally or horizontally (side-to-side) and distally/proximally (in and out), in relation to the mouth of the patient. Usually, the vertical, planar position of device 10 is maintained, whereby device 10 moves only in a single plane, and does not rise or fall, move up or down, or rotate or tilt during a scanning procedure.

As shown in the figures, nozzles 1-3 are deployed on the housing body 4 in such a way that pressurized air may be locally supplied in the oral region. The air is supplied from an external gas source outside device 10 via a connecting line which simultaneously or separately may supply pressurized air to all the nozzles (e.g., using corresponding ducts or canals).

The nozzles are configured in such a way that prior to the collection of the 3D measured or scanned data in a specific region, an air stream provided through leading nozzle 1 first cleans that region, by causing any particles/saliva or discharged blood presented in that region to be removed. As a result, during the collection of the 3D measured or scanned data, nozzles 2 and 3 cause air stream to diffuse around the entire periphery of the region of a portion of a tooth that is already cleaned by leading nozzle 1.

The air stream provided by nozzles 2 and 3 causes that a type of pocket or groove is formed between the gingiva and the tooth. Thereby, a valid collection of 3D measured or scanned data is enabled, so that the transition region, which is normally covered by the tooth via the gingiva, may be recorded.

According to an embodiment of the invention, in order to maintain the exposed elements of imaging unit 5 in an optimal condition when removing oral particles such as any blood, saliva or other residues, prior to the imaging of the tooth, leading nozzle 1 supplies the pressurized air to each region in a perpendicular manner with respect to the top crown surface of the tooth and before imaging unit 5 scans that region. The pressurized, air is applied to the region vertically, i.e. perpendicular to the surface and region that is to be inspected by the imaging unit 5, in order to remove the residues to the sides of the region so that they will not cover the imaging unit 5 when activated along with nozzles 2 and 3. For example, nozzle 1 can be located at the bottom of the housing body 4 distal to the location of imaging unit 5 with respect to the distally/proximally (in and out) movement of the intraoral scanner (as shown in the figures).

According to another embodiment of the invention, device 10 further comprises an additional air nozzle 1a for removing residue on the proximal side of imaging unit 5, opposite to air nozzle 1, as is shown in FIGS. 1 and 2. Nozzle 1a can be used for removing residues, such as blood and saliva, from the proximal side of imaging unit 5 while nozzle 1 is used for removing residues from the distal side thereof. Nozzles 1 and 1a can be manually or automatically used separately or simultaneously. For instance, nozzle 1 can be used alone when device 10 is inserted to the mouth of a patient and during distal motion of device 10, while in contrast nozzle 1a can be used alone during proximal motion of device 10 as to ensure a clean region clearly obtaining optical data while device 10 moves in either direction.

According to an embodiment of the invention, nozzles 2 and 3 are located from both sides of the imaging unit 5. An individual air streams flows from each of both nozzles 2 and 3, and as a whole these nozzles essentially diffuse around the entire periphery of this region, and due to the supplied air pressure, the gingiva are pushed away slightly from the tooth, thus forming the pocket or groove and exposing the tooth at this location.

According to an embodiment of the invention, the arrangement of the nozzles may create a masking air wall that prevents blood or saliva to contaminate the optical elements.

Figure 3:
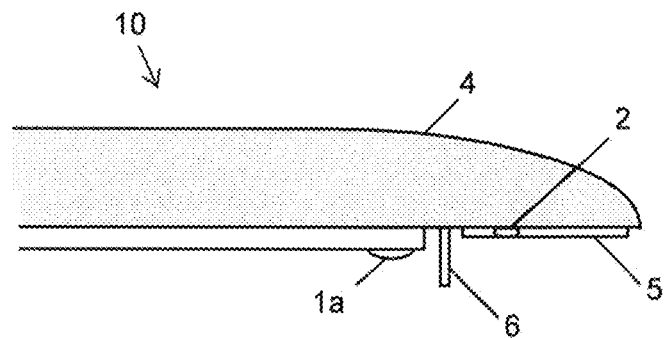
FIG. 3 schematically illustrates a side view of the tip of FIG. 1 provided a buffering wall for preventing the dirtying of the exposed elements of an imaging unit.
Figure 4:
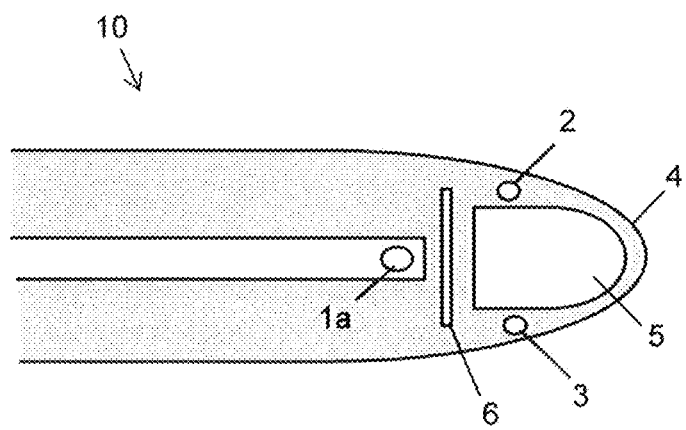
FIG. 4 schematically illustrates a bottom view of the tip of FIG. 3.

According to an embodiment of the invention, a buffering wall 6 is provided at the bottom of the housing body 4 of device 10 for preventing from oral particles such as saliva or discharged blood to reach the surface of a mirror or other optical element of imaging unit 5. For example, the optical element can be one or more lens/mirrors adapted to deliver images of the oral cavity to an imaging module of the intraoral scanner. As shown in FIGS. 3 and 4, the buffering wall 6 is located between nozzle 1a and imaging unit 5, such that an oral residual that might spread in that region (due to the pressurized air provided by nozzle 1a), may hit the buffering wall 6 but will not reach the elements of imaging unit 5.

In particular to control the air pressure in a targeted manner, for example to simultaneously form a pocket all the way around a tooth or to form larger and smaller pockets, it is practical for the air delivery device to be connected to a control device by means of which the quantity and/or pressure of the air supply may be adjusted.

According to an embodiment of the invention, for the targeted control of a given locally selectable oral region, device 10 may include a mechanism (not shown) adapted to adjust the position of one or more of the nozzles, thereby enabling to adjust the position of nozzles 2, 3 and/or nozzles 1 and 1a for the targeted delivery of air in a desired direction. Such an adjustment of the nozzles may be performed manually, for example before the intraoral scanning, depending on the particular design of the nozzle, or by use of a control device which is connected to the air delivery device (e.g., via electro-mechanical actuators).

Figure 5:
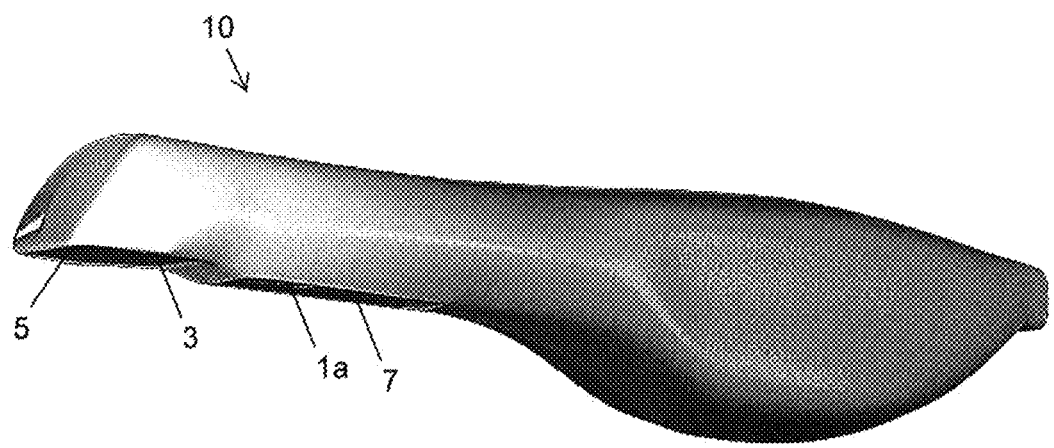
FIG. 5 shows an implementation of a tip for an intraoral scanner in a perspective view, according to an embodiment of the invention.
Figure 6:
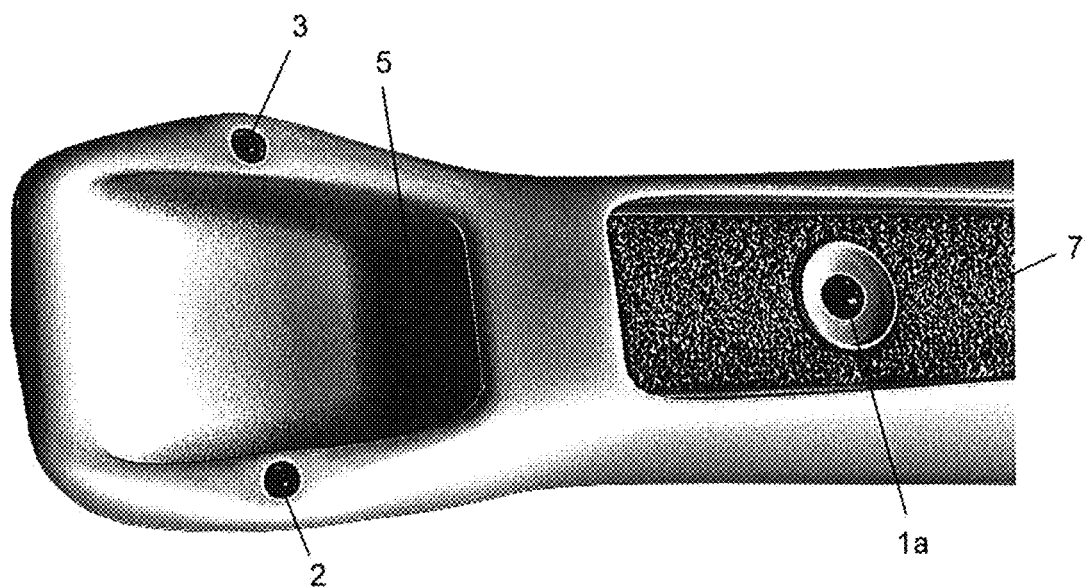
FIG. 6 shows a partial bottom view of the tip of FIG. 5.

Referring now to FIGS. 5 and 6, a possible implementation of device 10 is shown in accordance with an embodiment of the present invention.

According to an embodiment of the invention, device 10 further comprises an absorbing layer adapted to capture oral particles such as blood during the cleaning of the scanned region (e.g., as indicated by numeral 7 in FIGS. 5 and 6). The absorbing layer can be located on the housing body 4 in such a way that during the scanning session it faces toward the scanned region.

As best seen in FIG. 6, an absorbing layer 7 surrounds the leading nozzle 1/1a. The absorbing layer 7 can be disposable and/or replaceable. The absorbing layer 7 can be made of a flexible material (e.g., sponge), semi-rigid material or rigid material.

The housing body 4 can be molded or otherwise fabricated using plastic or other appropriate lightweight material, and can be formed as a single unit, or can be formed as sections, example upper and lower halves, which are fitted together to form the single housing body unit.

As will be appreciated by the skilled person the arrangement described in the figures results in a device which is capable of revealing covered teeth portions while applying in vivo scanning of dental structures to create a 3D model, while maintaining the optical elements in a clean condition According to an embodiment of the invention, a dedicated software module can be used to provide working instructions to the user/operator of the intraoral scanner during the entire scanning session. In one embodiment, images transferred from the tip to the imaging module of the intraoral scanner can be analyzed in real-time and accordingly be utilized in order to provide relevant guiding information to the user during the operation of the intraoral scanner (e.g., by applying suitable computer vision algorithms), an order to facilitate the scanning procedure. For example, the software module may include step-by-step instructions for enabling the user to perform an optimal scanning procedure.

All the above description and examples have been given for the purpose of illustration and are not intended to limit the invention in any way. Many different mechanisms can be employed, all without exceeding the scope of the invention.

The invention claimed is:

1. A tip for an intraoral scanner, comprising:
   a) a housing having an optical arrangement configured to transfer images of an oral region to an imaging module of the intraoral scanner;
   b) a first nozzle through which a first gas stream is applied, said first nozzle being oriented to extend downwards from a bottom of said housing to apply said first gas stream generally perpendicular with respect to the top crown surface of a tooth to remove oral particles from said oral region;
   c) a second nozzle through which a second gas stream is applied to expose a sub-gingival area of said oral region, said second nozzle being oriented to extend downwards from said bottom of said housing; and
   d) a buffering wall extending from said bottom of said housing, wherein said optical arrangement and said second nozzle are located on a first side of said buffering wall and wherein said first nozzle is located on a second side of said buffering wall, and wherein said buffering wall is oriented to shield said optical arrangement from the removed oral particles,
   wherein during use of the tip, said oral region is first exposed to said first gas stream and subsequently exposed to said second gas stream, thereby maintaining said optical arrangement and the oral region including the sub-gingival area thereof in a clean and dry condition during a scanning session.

2. The tip according to claim 1, further comprising an absorbing layer adapted to capture oral particles during the scanning session of a scanned region, wherein said absorbing layer is located on the housing in such a way that during the scanning session it faces toward the scanned region.

3. The tip according to claim 2, in which the absorbing layer is disposable and/or replaceable.

4. The tip according to claim 2, in which the absorbing layer is made of a flexible material, semi-rigid material or rigid material.

5. The tip according to claim 1, in which the gas is air or mixture of other gases.

6. The tip according to claim 1, in which the housing includes a connector to which a pressurized gas source is connected to supply the gas streams through at least one of said first and said second nozzle via one or more ducts or canals that transfers said gas from said source to said at least one of said first and said second nozzle.

* * * * *